United States Patent [19]

Aal et al.

[11] 3,945,891
[45] Mar. 23, 1976

[54] DISTILLATION PROCESS FOR PURIFICATION OF TRIARYL PHOSPHATE ESTERS

[75] Inventors: Robert A. Aal; Norman H. C. Chen; James K. Chapman, Jr., all of Yardley, Pa.

[73] Assignee: FMC Corporation, Philadelphia, Pa.

[22] Filed: June 20, 1974

[21] Appl. No.: 481,161

[52] U.S. Cl. .................. 203/77; 203/88; 203/91; 260/990
[51] Int. Cl.² ................. B01D 3/00; B01D 3/10
[58] Field of Search ........... 203/71, 73, 74, 77, 80, 203/81, 88, 89, 91; 260/990

[56] References Cited
UNITED STATES PATENTS

| | | |
|---|---|---|
| 2,272,193 | 2/1942 | Fisher et al. .................. 260/990 |
| 2,805,240 | 9/1957 | Prahl ............................ 260/990 |
| 3,219,547 | 11/1965 | Wheeler ........................ 203/77 |

*Primary Examiner*—Jack Sofer
*Assistant Examiner*—Frank Sever

[57] ABSTRACT

Crude phosphate ester products resulting from the phosphorylation of phenol, lower alkyl phenols and mixtures of same are purified to prepare triaryl phosphates substantially free of unreacted phenols by the sequential steps of flash distillation and fractional distillation under controlled conditions with removal of the phosphate ester product as a liquid underflow.

8 Claims, 1 Drawing Figure

U.S. Patent  March 23, 1976  3,945,891
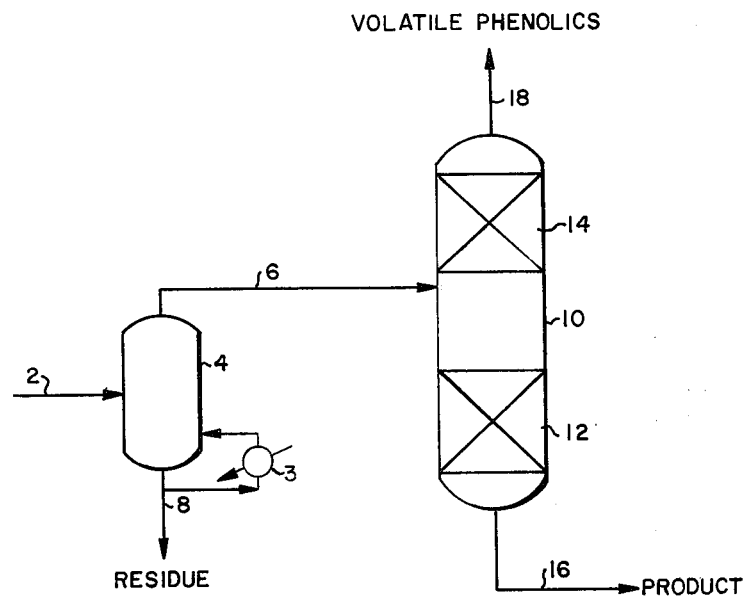

DISTILLATION PROCESS FOR PURIFICATION OF TRIARYL PHOSPHATE ESTERS

This invention relates to the purification of triaryl phosphate esters. More particularly, this invention relates to a novel, improved distillation process for the purification of triaryl phosphates so as to substantially eliminate the presence of unreacted phenolic contaminants.

Triaryl phosphate esters such as cresyl diphenyl phosphate, tricresyl phosphate, triphenyl phosphate, mixed xylyl cresyl phosphates, lower alkylphenyl/phenyl phosphates, such as mixed isopropylphenyl/phenyl phosphates, t-butylphenyl/phenyl phosphates, and the like are used extensively as plasticizers, functional fluids, gasoline additives, flame-retardant additives and the like. These products are conventionally prepared by the phosphorylation of a suitable phenolic feedstock, either the so-called natural cresols which are coal tar phenol fractions or synthetic feedstocks produced by alkylation of phenols as described, for example, in U.S. Pat. No. 3,576,923 issued April 27, 1971 to Randell et al.

Increasingly more stringent limitations are being placed upon the allowable amount of unreacted and/or free phenols in chemical products. These requirements have created a demand for manufactured triaryl phosphate ester products which contain only trace quantities of unreacted phenols and alkyl phenols. Heretofore commercially available triaryl phosphate ester products purified by distillation generally contain from about 500 to 3000 parts per million (ppm) of such phenols. The term "phenols" as used herein is meant to include not only phenol itself but also unreacted or free alkylated phenols containing one or more alkyl substituents, the alkyl groups each having about 1 to 4 carbon atoms. The term "free phenols" is employed to indicate that some phenols are formed as a result of decomposition reactions during purification as opposed to "unreacted phenols" which did not undergo phosphorylation.

Distillation processes for purification of triaryl phosphate esters are known and are disclosed, for example, in U.S. Pat. No. 3,219,547, issued Nov. 23, 1965 to Wheeler. Such conventional distillation processes are not capable of reducing the phenolic content to very low levels, that is, to a concentration of 100 parts per million or less. It is a current objective of those in the industry to produce commercially available triaryl phosphate esters which contain these minimal quantities of unreacted or free phenol or alkyl phenols, that is, less than 100 ppm.

Additional extensive treatments have been necessary, as supplements to conventional distillation techniques, to reduce the phenolic content of triaryl phosphates to very low levels. These techniques include caustic washing, permanganate oxidation, treatment with solid adsorbents and the like. Avoidance of these economically unattractive processing steps is achieved in the practice of the invention described hereinbelow.

In accordance with the present invention, there has been discovered an improved distillation process for the purification of crude triaryl phosphate esters prepared by the phosphorylation of phenol, $C_1$–$C_4$ alkyl substituted phenols and mixtures of same, comprising the steps of:

a. subjecting the crude triaryl phosphate ester reaction mixture to flash distillation at a temperature of from about 220° to 320°C and at a pressure of 2 to 10 mm. Hg and removing catalyst residues and high boiling impurities in an underflow and removing at least 90% by weight of the feedstock as overhead vapors comprising triaryl phosphate ester product and unreacted phenols, and b. fractionally distilling the overhead from the flash distillation step in a fractional distillation column having a low pressure-drop per theoretical stage maintained at a temperature of 250° to 300°C, a pressure of 4 to 10 mm. Hg at the base of said column and at a temperature of about 60° to 200°C and a pressure of 2 to 4 mm. Hg at the top of said column, and c. removing the purified triaryl phosphate ester product as a liquid underflow from the base of said column, the product being characterized as containing not more than about 100 parts per million of unreacted or free phenol or alkyl phenols.

The invention is generally applicable to the purification of triaryl phosphate esters produced by the phosphorylation of phenol and various mono- and polyalkylated phenols wherein the alkyl group contain from 1 to 4 carbon atoms, mixtures of alkyl phenols, and mixtures of phenol with alkyl phenols. Exemplary are phenol, ortho- meta- and para- cresols, the isomeric xylenols, the isomeric polymethyl phenols, ethylphenols such as tetraethyl phenols, alkylated phenols containing alkyl groups such as ethyl, isopropyl, n-propyl, tertiary butyl, secondary butyl and the like as well as mixtures of same and partially alkylated products such as mixtures of isopropylphenols or t-butylphenols and phenols produced by the propylene or isobutylene alkylation of phenol as described in said U.S. Pat. No. 3,576,923. The triaryl phosphate esters are produced by any suitable technique, typically by phosphorylation with $POCl_3$ in the presence of a Friedel-Crafts catalyst such as aluminum chloride.

In the process of the present invention, the crude phosphorylation reaction batch is first subjected to flash distillation. The flash distillation unit is generally operated with a reboiler temperature of 220° to 320°C with the pressure maintained at about 2 to 10 mm. Hg. Under these conditions, approximately 90 to 98% by weight of the crude ester feedstock is rapidly removed overhead, the overhead stream being principally unreacted free phenol and the desired triaryl phosphate product. Catalyst residue and other high boiling impurities are removed in an underflow which amounts to approximately 2 to 10% by weight, based on the weight of feedstock charged.

Catalyst residue, which comprises aluminum aryloxides and aluminum chloro-aryloxides, and other high boiling impurities dissolved in triaryl phosphates are removed as an underflow from the crude flash distillation unit. It is important that the catalyst residue be removed at this step of the process, during the crude flashing step. This technique enables a highly efficient fractional distillation to be carried out since the immediate withdrawal of the catalyst residues from the product stream reduces the probability of catalytic decomposition reactions which can result in the formation of increased amounts of phenols and prevents fouling of the fractionation device.

The distillate is generally condensed but may be allowed to remain in vapor form and is transferred to a fractionation column characterized as having a low pressure-drop throughout the column. The distillate is introduced at the column midpoint or above in order to promote stripping. The fractional distillation is carried out generally with the reboiler maintained at 250° to 300°C and at a pressure of 4 to 10 mm. Hg at the base of the column. At the top of the column, the pressure is maintained at about 2 to 4 mm. Hg with an overhead temperature of 60° to 200°C. A falling film reboiler is generally used to minimize residence time.

A highly significant aspect of the present invention is that exposure of triaryl phosphate ester product to high temperatures is minimized in order to prevent thermal decomposition of the ester product which can result in the production of additional free phenols. Precise maintenance of temperature and pressure conditions is required to ensure complete effectiveness of the process and to accomplish the desired objective of producing triaryl phosphate ester product having a free phenolic content of 100 ppm or less without the need for after-treatment process in order to prepare a commercial product of acceptable purity.

Fractional distillation under these conditions results in a highly efficient fractionation of the charge stream. Triaryl phosphate ester product so produced will contain generally less than 100 parts per million (ppm) of unreacted or free phenols. Preferably, there can be less than 50 ppm of such phenols with products having been obtained containing between 1 and 10 ppm of free phenols, or only trace quantities thereof. Heretofore, it has not been possible to produce triaryl phosphates with such low concentrations of phenolic contaminants in a distillation technique.

It is critical to the process of the present invention that the distillate product be removed as a liquid underflow from the fractionation column. This allows the volatile phenols to pass through the column in the vapor state. Removal of product as a vaporous stream would not accomplish the desired result, since this stream would contain relatively substantial amounts of phenolic contaminants.

The preferred temperature and pressure operating conditions for the flash distillation and fractional distillation steps, particularly the latter, will depend on the particular triaryl phosphate ester being treated in accordance with the present invention. The invention is especially suitable for the purification of triaryl phosphate esters used as plasticizers and functional fluids especially tricresyl phosphate, cresyl diphenyl phosphate, trixylyl phosphate and the mixed alkylphenyl/phenyl phosphates prepared by phosphorylation of an alkylate formed by reacting butylene, isobutylene or propylene in amounts of 10 to 40% with phenol. The latter products are mixed isopropylphenyl/phenyl phosphates, secondary-butylphenyl/phenyl phosphates and tertiarybutylphenyl/phenyl phosphates as described, for example, in U.S. Pat. Nos. 3,576,923, issued Apr. 27, 1971 to Randell et al. and 3,533,155, issued Jan. 5, 1971 to Garrett. Such mixed products generally contain about 30 to 50% phenyl groups and 70 to 50% alkylphenyl groups.

For flash distillation, a preferred temperature range of 250°–310°C and a pressure range of 5 to 8 mm. Hg applies to all triaryl phosphates. The preferred fractional distillation conditions for isopropylphenyl/phenyl phosphate products are a reboiler temperature of 255° to 275°C and a base pressure of 5.4 to 9 mm. Hg. For the distillation of phosphorylated isobutylene-phenol alkylation products, the preferred ranges for fractional distillation are a reboiler temperature of 270° to 275°C and a base pressure of 8 to 9 mm. Hg. For cresyl diphenyl phosphate preferred fractional distillation reboiler conditions will be 4.9–8.1 mm. Hg and 252° to 266°C. For tricresyl phosphate, fractional distillation is preferably carried out with reboiler temperatures at 258° to 278°C and a base pressure of 5.4 to 6.6 mm. Hg. For trixylyl phosphate, optimum fractional distillation conditions are a reboiler pressure of 4.8 to 7.3 mm. Hg and a reboiler temperature of 271° to 282°C.

The fractional distillation is carried out using a fractionating device for high vacuum distillation characterized as having a low pressure drop per theoretical stage. Particularly suitable are packed fractionation columns containing predominantly filmwise contacting devices where capillary action predominates. Packing sections suitable for such high vacuum distillation are generally prepared from corrugated woven wire fabric, rolled screen, closely spaced vertical coils or springs, knitted multi-filament packing and the like, with the packing sections being stacked vertically in the column. Particularly suitable are cylindrical packing sections formed from stainless steel woven fine wire fabric. The circular sections have the same diameter as the column and are stacked in the column in layers. Also suitable, but less preferable, are the dropwise contacting devices such as fractionators containing a plurality of impellers on a rotating shaft, or differential evaporation devices containing an internally cooled central rotor having attached vertical blades, wherein fractionation occurs through the repeated processes of evaporation and condensation.

The fractional distillation is usually operated with a reflux ratio of about 0.5:1 to 1.5:1. However, the process can be carried out without any reflux and in this case the overhead temperature will be at the higher end of the range described, that is, from about 90°C up to about 150°C, that is, about or higher, up to about 200°C. This may be done when it is desired to improve the color of the product.

The liquid underflow product triaryl phosphate ester produced in accordance with the present invention meets most current product specifications for use as functional fluids or plasticizers. However, for certain applications, further treatment of the product may be desirable. For example, when plasticizer grade products having a color of 50 APHA (ASTM D-1209-62) or less are desired, a supplemental flash distillation of the product may be carried out at about 245° to 255°C and 2 to 4 mm. Hg.

The drawing illustrates diagrammatically the purification procedure of this invention. In the drawing a crude triaryl phosphate ester reaction mixture is passed through line 2 into flash distiller 4 operated with a reboiler 3 at a temperature of about 220° to 320°C at about 2 to 10 mm Hg. Catalyst residues and other high boiling impurities are removed as an underflow through line 8 from distiller 4. The catalyst residues are not passed to fractional distillation column 10 in order to reduce catalytic decomposition reactions which result in the formation of increased amounts of phenols. An overhead stream principally containing unreacted free phenol and the desired triaryl phosphate ester product is removed through line 6 and passed to fractional distillation column 10, entering the column midpoint or above in order to promote stripping. Fractional distillation of the unreacted free phenol and the desired triaryl phosphate ester product is carried out in fractional distillation column 10. Fractional distillation is carried out at 250° to 300°C and at a pressure of 4 to 10 mm Hg at column base 12 while column top 14 is at a temperature of 60° to 200°C and at a pressure of 2 to 4 mm Hg. Precise maintenance of temperature and pressure conditions is required to produce a triaryl phosphate ester product having a free phenolic content of 100 ppm or less without the need for an after-treatment process. The product is removed from column 10 as a liquid underflow through line 16. Volatile phenolics pass through column 10 in the vapor state and are removed through overhead line 18. Removal of the triaryl phosphate ester product as a sidestream rather than as a liquid underflow would result in a product having a substantial amount of phenolic contaminants.

The invention is further illustrated by the following examples which are not to be considered limitative of its scope. Parts and percentages reported are by weight unless otherwise indicated.

EXAMPLE I 13,000 parts of an isopropylphenol/phenol mixture prepared by alkylating phenol with about 28 to 30% by weight propylene were mixed with 65 parts $AlCl_3$ and stirred with heating to 120°C, 4,558 parts of $POCl_3$ were added over a period of 2 hours. The reaction mixture was heated slowly to 220°C over a period of 4½ hours held at 220°C for 1½ hours then cooled to room temperature to form a mixed isopropylphenyl/phenyl phosphate.

The crude products were fed to flash distillation apparatus comprising a graduated adding funnel, flowmeter preheater, thermal siphon reboiler equipped with electrical heater and level controller, vapor line and condensing system connected to a vacuum source, and a device for continuous bottoms draw. The product was fed to the crude flasher at a rate of about 5.3 pounds per hour, flash distillation was conducted at pressure of 7 mm. Hg, reboiler temperature of 260° to 270°C, an overhead temperature of 250° to 260°C. 5% of the feedstock was continuously removed as an underflow. The flash distillate was then continuously fractionally distilled.

The fractionation unit comprised a flow-controlled feed system, preheater, vacuum jacketed glass column packed with 9 stainless steel cylindrical packing sections (thickness to 6.8 inches; diameter 1.6 inches) formed from parallel corrugated strips of woven stainless steel wire fabric, vapor line with condenser, reflux return, automatic reflux ratio controller, condensate take-off and receiver, and an electrically heated thermal siphon reboiler. The distillate was fed at a point 2 sections from the top of the column at about 5 pounds per hour. Overhead pressure was 2 to 3 mm. Hg; reboiler pressure was 6 to 7 mm. Hg. The overhead temperature range was 85° to 90°C and the reboiler temperature was 260° to 270°C. The reflux ratio was generally 0.5 to 1. Under these conditions, the overhead vapor was substantially free of phosphate esters, while the triaryl phosphate ester product was removed as a liquid underflow and contained from about 2 to 3 ppm unreacted phenols as determined by gas chromatography. The underflow product had a color of 90 to 50 APHA; acidity (as acetic acid) 0.003–0.005%; passed the hydrolytic stability test (ASTM D-2619-67) and had a viscosity of 49.5 centistokes at 100°F.

EXAMPLE II

Under a nitrogen blanket and a glass reactor were charged 10,000 parts of meta/paracresols and 25 parts of $AlCl_3$. The mixture was stirred and heated to 120° and $POCl_3$, 4,420 parts, was added uniformly over a period of 2½ hours. The temperature was then gradually raised to 220°C over an additional period of 1½ hours and then held at 220°C for 1½ hours.

The crude product so obtained was continuously flashed distilled by employing the equipment described in Example I. Conditions were as follows: a feed rate of 5.5 pounds per hour, a pressure of 7 mm. Hg, a reboiler temperature of 265° to 275°C, an overhead temperature of 255° to 265°C and an underflow draw rate of 5% by weight.

The flash distillate was continuously fractionally distilled as in Example I. The operating conditions were: a feed rate of 4 to 5 pounds per hour, an overhead pressure of 3 mm. Hg, a reboiler pressure of 6.5 mm. Hg, an overhead temperature of 65° to 75°C, a reboiler temperature of 265° to 275°C and a reflux ratio of 1.1–1.5 to 1.

The triaryl phosphate ester product was removed as a liquid underflow and the product was analyzed as containing from 3 to 30 ppm of free unreacted phenols. Other properties were as follows: color 90–150 A.P.H.A., acidity 0.01% (as acetic acid) and specific gravity 1.171.

Reducing or eliminating the reflux return and raising the overhead temperature to 100° to 150°C improved the color of the underflow product to 50–60 A.P.H.A. while maintaining free phenol level at 3 to 8 ppm without affecting any other properties.

EXAMPLE III

An alkylated phenol mixture was prepared by reacting phenol with 20% by weight isobutylene and phosphorylated by the method of Example I using 0.5% $AlCl_3$ and 95% of the theoretically stoichiometric amount of $POCl_3$. A mixed tertiary-butylphenyl/phenyl phosphate was produced.

The crude product so obtained was continuously flash distilled as described in Example I. Operating conditions were:

| | |
|---|---|
| Feed rate | 6.5 lbs/hr. |
| Pressure | 6.0 mm. Hg |
| Reboiler temp. | 283–291°C |
| Overhead temp. | 274–280°C |
| Underflow draw rate | 5.2% |

The flash distillate was continuously fractionated as described in Example I, operating conditions are summarized as follows:

| | |
|---|---|
| Feed rate | 6.2 lbs/hr. |
| Overhead pressure | 3.4 mm. Hg |
| Reboiler pressure | 8.6 mm. Hg |
| Overhead temp. | 87–89°C |
| Reboiler temp. | 273–274°C |
| Reflux ratio | 1:1 |

The underflow product obtained under these conditions contained 9 ppm of free phenols and had a color of 250 APHA.

EXAMPLE IV

A mixed isopropylphenyl/phenyl phosphate prepared by phosphorylation of a phenol propylated with about 30% by weight propylene was distilled as described in Example I. The fractional distillation column was provided with a device for taking a vapor sample at the bottom of the column in order to compare the phenolic content of vaporous sidestream samples with product removed as a liquid underflow. The results are tabulated below:

| Sample No. | Free Phenols - ppm Vapor | Liquid |
|---|---|---|
| (a) | 212 | 81 |
| (b) | 303 | 95 |
| (c) | 135 | 54 |
| (d) | 121 | 97 |
| (e) | 64 | 32 |
| (f) | 89 | 78 |

What is claimed is:

1. A process for purifying triaryl phosphate esters prepared by the phosphorylation of phenol, $C_1$–$C_4$ alkyl substituted phenols and mixtures of same consisting essentially of:
   a. subjecting the crude triaryl phosphate ester reaction mixture of flash distillation at a temperature of about 220° to 320°C and a pressure of 2 to 10 mm. Hg and removing catalyst residues and high boiling impurities in an underflow and removing at least 90% of the feedstock as an overhead distillate comprising triaryl phosphate ester product and unreacted phenols, and
   b. fractionally distilling the overhead from the flash distillation step in a fractional distillation column having a low pressure drop per theoretical stage maintained at a temperature of about 250° to 300°C and at a pressure of 4 to 10 mm. Hg at the base of said column and a temperature of about 60° to 200°C and a pressure of 2 to 4 mm. Hg at the top of said column, and
   c. removing the purified triaryl phosphate ester product as a liquid underflow from the base of said column, the product being characterized as containing less than about 100 parts per million of unreacted phenols, free phenol, and alkyl phenols.

2. The process of claim 1 wherein said phosphate ester is a mixed isopropylphenyl/phenyl phosphate.

3. The process of claim 1 wherein said phosphate ester is a mixed secondary-butylphenyl/phenyl or tertiarybutylphenyl/phenyl phosphate.

4. The process of claim 1 wherein said phosphate ester is cresyl diphenyl phosphate.

5. The process of claim 1 wherein said phosphate ester is tricresyl phosphate.

6. The process of claim 1 wherein said phosphate ester is trixylyl phosphate.

7. The process of claim 1 wherein said purified triaryl phosphate ester is characterized as containing less than 50 ppm of said free, phenol, unreacted phenols, and alkyl phenols.

8. The process of claim 1 wherein the flash distillation is carried out at a temperature of 250° to 310°C and a pressure of 5 to 8 mm. Hg.

* * * * *

UNITED STATES PATENT OFFICE
CERTIFICATE OF CORRECTION

PATENT NO. : 3,945,891

DATED : March 23, 1976

INVENTOR(S) : ROBERT A. AAL, NORMAN H. C. CHEN and JAMES K. CHAPMAN, JR.

It is certified that error appears in the above-identified patent and that said Letters Patent are hereby corrected as shown below:

Column 3, line 57 "3,533,155" should read --3,553,155--.

Column 7, line 29 "of" should read --to--.

Column 8, line 29 "free, phenol" should read --free phenol--.

Signed and Sealed this

Twenty-eighth Day of December 1976

[SEAL]

Attest:

RUTH C. MASON
Attesting Officer

C. MARSHALL DANN
Commissioner of Patents and Trademarks